(12) United States Patent
Chen et al.

(10) Patent No.: US 11,348,551 B2
(45) Date of Patent: May 31, 2022

(54) MONITOR, DISPLAY DEVICE THEREOF, AND MONITORING SYSTEM

(71) Applicant: SHENZHEN MINDRAY BIO-MEDICAL ELECTRONICS CO., LTD., Shenzhen (CN)

(72) Inventors: Dabing Chen, Shenzhen (CN); Lian Hu, Shenzhen (CN); Xuegang Zhang, Shenzhen (CN); Liang Zhao, Shenzhen (CN); Wei Chen, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 0 days.

(21) Appl. No.: 17/094,456

(22) Filed: Nov. 10, 2020

(65) Prior Publication Data
US 2021/0125576 A1    Apr. 29, 2021

Related U.S. Application Data

(63) Continuation of application No. 16/848,572, filed on Apr. 14, 2020, now Pat. No. 10,832,629, which is a
(Continued)

(51) Int. Cl.
*G09G 5/00* (2006.01)
*A61B 5/00* (2006.01)
(Continued)

(52) U.S. Cl.
CPC ............... *G09G 5/003* (2013.01); *A61B 5/00* (2013.01); *F16M 11/04* (2013.01);
(Continued)

(58) Field of Classification Search
CPC ............ G09G 5/003; G09G 5/14; G09G 5/38; G09G 2340/0492; G09G 2380/08;
(Continued)

(56) References Cited

U.S. PATENT DOCUMENTS 5,187,641 A   2/1993   Muskatello et al.
5,329,289 A   7/1994   Sakamoto et al.
(Continued)

FOREIGN PATENT DOCUMENTS

CN   201146061   11/2008
CN   101566264   10/2009
(Continued)

*Primary Examiner* — Muhammad Ijaz
(74) *Attorney, Agent, or Firm* — Kory D. Christensen

(57) ABSTRACT

The display device may include a display unit and a support unit. The display unit is used for displaying patient-end parameter information. The support unit comprises an adapter cover and a rotating unit connected onto the adapter cover. The display unit is fastened and connected onto the adapter cover in a way that allows rotation relative to the rotating unit. The monitor comprises: a master control unit and the display unit, where the master control unit is connected to a patient end via at least one cable, and the display unit is detachably connected to the master control unit. With the implementation of the monitor, the display device thereof, and the monitoring system, the display unit rotates and switches while the position of the connecting cable of the master control unit remains unchanged; corresponding marker display areas and alarm light display areas are lit up after rotating and switching in order to taking into consideration habits of a user.

20 Claims, 5 Drawing Sheets

Related U.S. Application Data continuation of application No. 15/917,368, filed on Mar. 9, 2018, now Pat. No. 10,621,946, which is a continuation of application No. PCT/CN2016/070188, filed on Sep. 16, 2015.

(51) Int. Cl.

| | | |
|---|---|---|
| *F16M 11/20* | (2006.01) | |
| *F16M 11/04* | (2006.01) | |
| *F16M 11/10* | (2006.01) | |
| *F16M 13/02* | (2006.01) | |
| *G09G 5/14* | (2006.01) | |
| *G09G 5/38* | (2006.01) | |
| *G16H 40/63* | (2018.01) | |

(52) U.S. Cl.
CPC ....... *F16M 11/105* (2013.01); *F16M 11/2014* (2013.01); *F16M 11/2021* (2013.01); *F16M 13/02* (2013.01); *G09G 5/14* (2013.01); *G09G 5/38* (2013.01); *F16M 2200/068* (2013.01); *G09G 2340/0492* (2013.01); *G09G 2380/08* (2013.01); *G16H 40/63* (2018.01)

(58) Field of Classification Search
CPC .. F16M 11/105; F16M 13/02; F16M 11/2021; F16M 2200/068; A61B 5/00; G16H 40/63
USPC .......... 248/121, 123.11, 917, 918, 919, 920; 600/300, 301; 345/659; 348/14.03
See application file for complete search history.

(56) References Cited

U.S. PATENT DOCUMENTS

| | | | | |
|---|---|---|---|---|
| 7,410,138 | B2* | 8/2008 | Parsons | F16M 11/24 248/125.7 |
| 7,430,113 | B2* | 9/2008 | McRight | F16M 11/105 361/679.55 |
| 9,254,104 | B2 | 2/2016 | Judy | |
| 9,355,219 | B2 | 5/2016 | Paydar | |
| 2006/0033847 | A1 | 2/2006 | Kim | |
| 2006/0243869 | A1 | 11/2006 | Petrick | |
| 2007/0185390 | A1* | 8/2007 | Perkins | A61B 5/02055 600/300 |
| 2008/0108884 | A1 | 5/2008 | Kiani | |
| 2011/0054267 | A1* | 3/2011 | Fidacaro | A61B 5/0002 600/300 |
| 2012/0127103 | A1* | 5/2012 | Qualey | A61B 5/742 345/173 |
| 2013/0109928 | A1* | 5/2013 | Menzel | G16H 40/63 600/301 |
| 2014/0022187 | A1* | 1/2014 | Jeong | G06F 3/041 345/173 |
| 2014/0276934 | A1 | 9/2014 | Balaji et al. | |
| 2014/0362117 | A1* | 12/2014 | Paulson | G06F 3/017 345/659 |
| 2016/0312946 | A1* | 10/2016 | Chang | F16M 13/02 |
| 2018/0226050 | A1* | 8/2018 | Chen | F16M 11/2021 |
| 2019/0317549 | A1* | 10/2019 | Gurr | F16M 11/105 |
| 2019/0318710 | A1* | 10/2019 | Gurr | F16M 11/046 |

FOREIGN PATENT DOCUMENTS

| | | |
|---|---|---|
| CN | 101940500 | 1/2011 |
| CN | 103181752 | 7/2013 |
| CN | 104887202 | 9/2015 |
| DE | 102007050060 A1 | 4/2009 |
| EP | 1110507 | 6/2001 |
| EP | 1401200 A2 | 3/2004 |

\* cited by examiner

MONITOR, DISPLAY DEVICE THEREOF, AND MONITORING SYSTEM

CROSS-REFERENCE TO RELATED APPLICATIONS

This application is a continuation of U.S. patent application Ser. No. 16/848,572, filed Apr. 14, 2020, for "MONITOR, DISPLAY DEVICE THEREOF, AND MONITORING SYSTEM," which is a continuation of U.S. patent application Ser. No. 15/917,368, filed Mar. 9, 2018, for "MONITOR, DISPLAY DEVICE THEREOF, AND MONITORING SYSTEM," now U.S. Pat. No. 10,621,946, which is a continuation of PCT Application No. PCT/CN2016/070188, filed Sep. 16, 2015, each of which is incorporated herein by reference.

TECHNICAL FIELD

The present disclosure relates to the field of medical devices, and in particular to a monitor, a display device thereof, and a monitoring system.

BACKGROUND ART

Conventionally, patient monitoring devices, especially monitors of a large size (17 inches or above), generally have a 16:9, 16:10, or 4:3 aspect ratio, and are usually placed in a landscape orientation. The landscape orientation has the advantage that very long waveforms can be displayed for certain parameters, such as ECG. In some cases, it is necessary to display long waveforms.

However, if it is needed to display multiple parameters, e.g., to display 16 or more waveforms, the above landscape display mode will have limitations and cannot conveniently display all parameter waveforms. In this case, more waveforms can be displayed if a portrait orientation is used. In many cases, it is more important for a display screen of a monitoring device to display more waveforms than to display longer waveforms. Therefore, it is necessary to choose a suitable orientation according to clinical application requirements.

With respect to the display devices of some existing monitors, although the display screen has the function of switching between landscape and portrait orientations, e.g., by rotating the whole monitor, such flexibility has its drawbacks. One problem is cable management in the above switching mode. Many cables are attached behind a host machine, so that when the monitor rotates 180 degrees, it is not available to a user because the cables cannot rotate or bend; or the cables are damaged quickly. If the display screen is provided with an interface (such as a USB interface), it is possible to damage the device connected to the USB interface.

SUMMARY

The technical problem to be solved by the present disclosure is to provide a monitor, a display device thereof, and a monitoring system, in which a display unit rotates and switches while the position of a connecting cable of a master control unit remains unchanged; and corresponding marker display areas and alarm light display areas are lit up after rotating and switching in order to take into consideration habits of a user. The disclosed system is structurally reasonable and facilitates assembly and maintenance.

In order to solve the above technical problem, an embodiment of the present disclosure provides a display device for a monitor, the display device comprising a display unit and a support unit, the display unit being used to display patient-end parameter information, and the display unit being fastened and connected to the support unit in a way that allows rotation relative to the support unit.

The support unit may include an adapter cover and a rotating unit connected to the adapter cover, and the display unit is rotatably connected to the rotating unit.

The rotating unit may include an assembling plate capable of being fastened to the adapter cover and a rotating head rotatably connected to the assembling plate; the display unit, the adapter cover, the assembling plate and the rotating head are assembled as a whole piece; and the assembled whole piece of the display unit, the adapter cover and the assembling plate rotates and switches between transverse or longitudinal directions relative to the rotating head.

The support unit may further include a support fastened and connected to the rotating head.

The display unit can be assembled on the adapter cover in either transverse or longitudinal direction.

The back of the display unit is provided with a plurality of connecting poles which are arranged in centrosymmetric distribution, the adapter cover is provided with assembling holes, and the display unit is fastened to the adapter cover in such a way that the plurality of centrosymmetric connecting poles are adaptively connected to the assembling holes in the transverse or longitudinal direction.

The display device may further include a master control unit which is integrally connected with the display unit and used for transmitting parameter information from a patient-end to the display unit, the display unit being detachably connected to the master control unit, and the bottom of the master control unit being fixedly provided with any of a power cable, a card cage cable, a subordinative screen cable, a USB connecting cable or a network signal cable to be connected to the patient-end.

The back of the display unit is provided with a plurality of connecting poles which are arranged in centrosymmetric distribution, the master control unit is provided with assembling holes, and the display unit is fastened to the master control unit in such a way that the plurality of centrosymmetric connecting poles are adaptively connected with the assembling holes in the transverse or longitudinal direction.

The display device may further include a master control unit which is integrally connected with the display unit and used for transmitting parameter information from a patient-end to the display unit, the master control unit being fastened to the rotating unit.

Short edges of the display unit are respectively provided with a first marker display area and/or an alarm light display area for displaying when the display unit is in a vertical mode, and long edges of the display unit are respectively provided with a second marker display area and/or an alarm light display area for displaying when the display unit is in a transverse mode.

In one embodiment, present disclosure also includes a monitor comprising a master control unit and a display unit, the master control unit being used for transmitting parameter information from a patient-end to the display unit, and the display unit being used for displaying the parameter information, wherein the master control unit is connected to the patient-end through at least one cable, and the display unit is detachably connected to the master control unit.

When the display unit and the master control unit are installed in such a way that a long edge of the display unit is disposed horizontally, the display unit is divided into N display areas parallel to the long edge, with waveforms/values related to the parameter information being displayed in at least one of the display areas; and when the display unit and the master control unit are installed in such a way that a short edge of the display unit is disposed horizontally, the display unit is divided into M display areas parallel to the short edge, with waveforms/values related to the parameter information being displayed in at least one of the display areas.

When the display unit and the master control unit are installed in such a way that a long edge of the display unit is disposed horizontally, waveforms related to the parameters are displayed in a first time zone, and when the display unit and the master control unit are installed in such a way that a short edge of the display unit is disposed horizontally, waveforms related to the parameters are displayed in a second time zone, the first time zone being greater than the second time zone.

In one embodiment, the number of the display areas N is less than the number of the display areas M.

The display unit may further include adaptively adjusted marker display areas and/or alarm light display areas. When the display unit and the master control unit are installed in such a way that a long edge of the display unit is horizontally disposed, the marker display areas and/or the alarm light display areas are lighted in the direction of the long edge; and when the display unit and the master control unit are installed in such a way that a short edge of the display unit is horizontally disposed, the marker display areas and/or the alarm light display areas are lighted in the direction of the short edge.

A connection cable for data transmission is provided between the master control unit and the display unit, and the connection cable is received inside the master control unit and the display unit.

The monitor may further include at least one parameter module for collecting at least one piece of parameter information about patients and transmitting the parameter information to the master control unit.

The present disclosure may also include a monitoring system comprising a master control unit and a display unit, the master control unit being used for transmitting parameter information from a patient-end to the display unit, and the display unit being used for displaying the parameter information, wherein the master control unit is connected to the patient-end through at least one cable, the display unit and the master control unit are separated from each other, and the display unit is rotatably installed on a support unit.

The display unit can be switched between landscape and portrait orientations by rotation.

When the display unit is switched between landscape and portrait orientations, the display unit is switched into a display mode correspondingly to keep the parameter information displayed in the horizontal direction.

The display unit may further include a marker display area and/or an alarm light display area, and when the display unit is switched between landscape and portrait orientations, the marker display area and/or the alarm light display area is/are switched into a display mode correspondingly to keep displaying in the horizontal direction.

The display unit may include a first group of marker display areas and/or one alarm light display area and a second group of marker display areas and/or one alarm light display area, the first group of marker display areas and/or one alarm light display area being disposed along a short edge of the display unit, and the second group of marker display areas and/or one alarm light display area being disposed along a long edge of the display unit, and when the display unit is switched to the portrait orientation, the master control unit controlling the first group of marker display areas and/or one alarm light display area to be effective while the second group of marker display areas and/or one alarm light display area to be ineffective.

The present disclosure also includes monitor comprising a display unit which can perform an in-plane rotation in the display unit's display surface.

The monitor may further include an installation portion which is connected to the display unit in a way that allows rotation.

The installation portion is connected to a support unit.

The monitor may further include a host machine which is independent of the display unit and cannot rotate with the display unit.

The monitor, the display device thereof and the monitoring system provided by the present disclosure have the following beneficial effects. First, the display unit and the master control unit are separated from each other, and the display unit is fastened and connected to the support unit in such a way that the display unit allows rotation relative to the rotating unit, so as to achieve the function of switching between transverse and longitudinal rotations. As a result, during the rotation of the display unit, the positions of cables of the master control unit do not change, so as to reduce the problems of entanglement and loosening of cables in a clinical setting. It is possible to prolong the service life of cable interfaces and devices, and serviceability is improved.

Second, after rotating and switching, the direction of screen rotation is automatically identified, and corresponding marker display areas and alarm light display areas are lit up in order to take into consideration habits of a user.

Third, with the integrated structure of the display unit and the master control unit, the used space can be reduced, and screen installation in the landscape or portrait orientation can be provided according to the actual application requirements, and since the positions of cables of the master control unit do not change, the connection mode of a signal line or a power line is not affected.

Finally, the embodiments disclosed herein are structurally reasonable, and facilitate assembly and maintenance.

DETAILED DESCRIPTION

The technical solutions of the embodiments of the present application will be described below clearly and comprehensively in conjunction with the drawings. The embodiments described are merely some embodiments of the present disclosure and are not all of the possible embodiments. Based on the embodiments given in the present disclosure, all other embodiments that would be obtained by those of ordinary skill in the art without expending inventive effort shall all fall within the scope of protection of the present disclosure.

As shown in FIGS. 1-5, one embodiment of a monitor according to the present disclosure is provided.

The monitor in this embodiment may include a display device (the portion by dotted lines shown in FIG. 1) and a master control unit 9 separately connected to the display device. The master control unit 9, as a host machine of the monitor, may include one or more interfaces connected with various parameter sensors or may include one or more interfaces connected with parameter modules. In this embodiment, the display device and the master control unit 9 are in wired connection through cables to transmit data or signals. In addition, the bottom of the master control unit 9 is fixedly provided with one or more cables for the connection with a patient-end. The cables include, but are not limited to, a power cable, a card cage cable, a subordinative screen cable, a USB connecting cable, a network signal cable, etc. and are marked as "L" in FIG. 1.

The monitor may further include at least one parameter module for collecting at least one piece of parameter information about patients and transmitting the parameter information to the master control unit 9.

Figure 1:
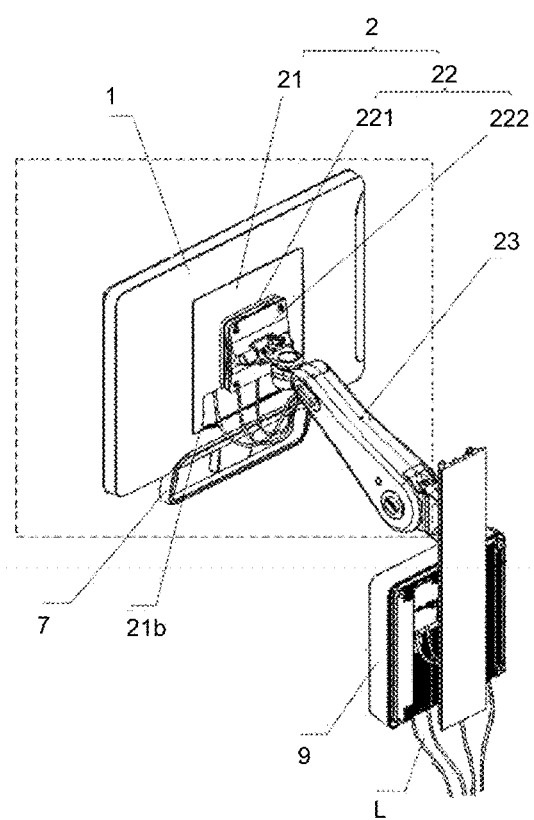
FIG. 1 is a schematic diagram of a local structure of a monitor.
Figure 2:
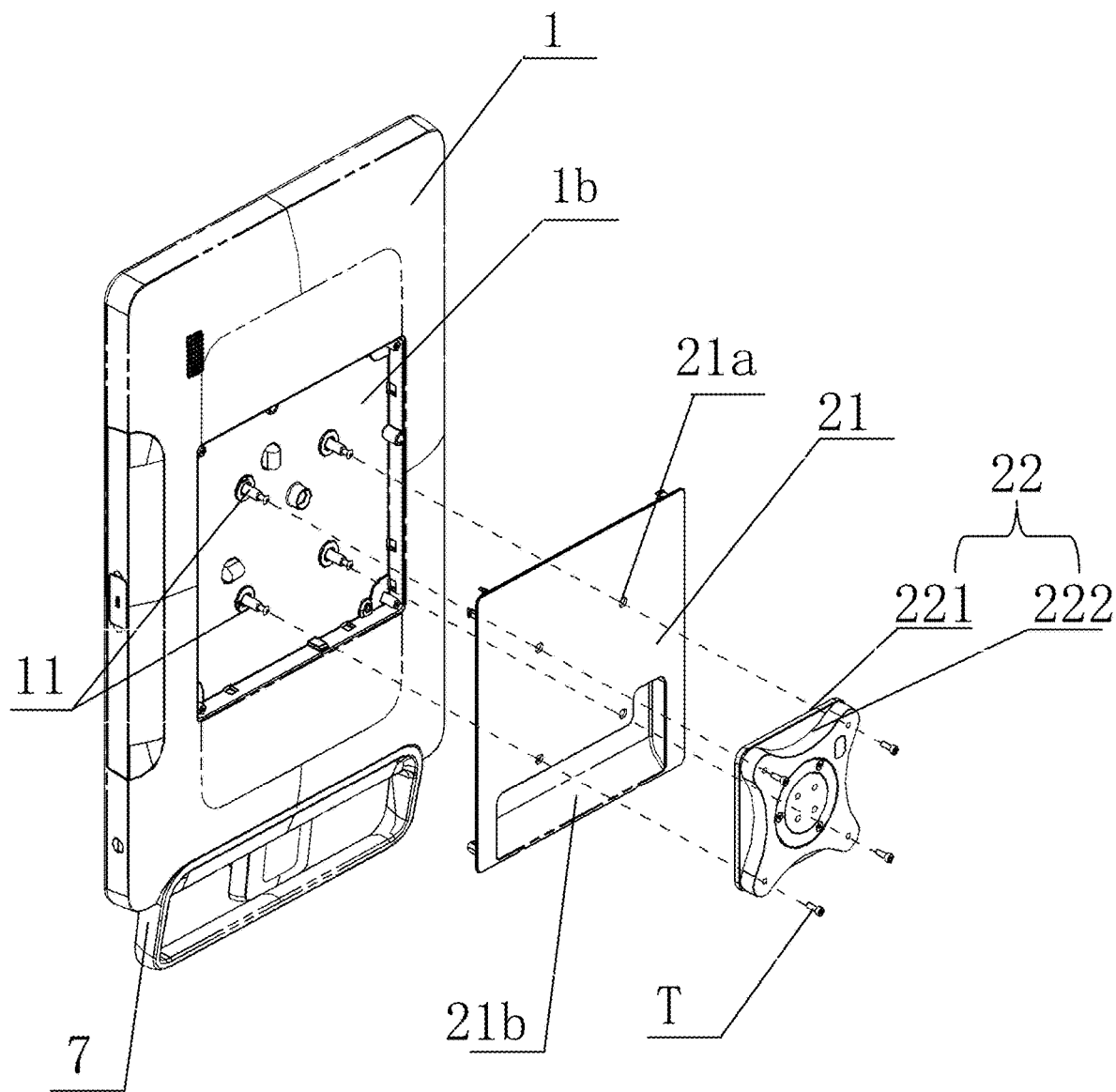
FIG. 2 is a schematic diagram of an assembled structure of a display device of the monitor.

As shown in FIG. 2, the display device may further include a display unit 1 for displaying patient-end parameter information and a support unit 2 for supporting the display unit 1. The master control unit 9 is used for transmitting the parameter information from the patient-end to the display unit 1, and the display unit 1 is used for displaying the parameter information acquired by the parameter module under the control of the master control unit 9. The display unit 1 has a display surface which is generally a flat surface, and a curved surface may also be chosen for display.

The support unit 2 may include an adapter cover 21 and a rotating unit 22 connected to the adapter cover 21. The display unit 1 is fastened and connected to the adapter cover 21 in a way that allows rotation relative to the rotating unit 22. The rotating unit 22 may include an assembling plate 221, which can be fastened to the adapter cover 21, and a rotating head 222, which is rotatably connected to the assembling plate 221. The display unit 1, the adapter cover 21, the assembling plate 221, and the rotating head 222 may be assembled as a whole piece.

Specifically, the back of the display unit 1 is provided with a cubic concave cavity 1b for assembly. A plurality of connecting poles 11 are arranged in the concave cavity 1b. In this embodiment, provided are four connecting poles 11 which are arranged at equal intervals and in a square shape, and moreover, the adapter cover 21 is in a square plate shape and can be exactly received in the above concave cavity 1b. The four corners of the adapter cover 21 are provided with assembling holes 21a, and the assembling holes 21a are provided at the positions completely corresponding to the positions of the plurality of connecting poles 11. In addition, the assembling plate 221 and the rotating head 222 are also respectively provided with screw holes or assembling holes (not shown) corresponding to the positions of the aforementioned connecting poles 11. In this way, during specific assembly, the connecting poles 11 can respectively pass through the assembling hole structures at the corresponding positions, and the display unit 1, the adapter cover 21, the assembling plate 221 and the rotating head 222 can be assembled as a whole piece through the locking engagement with screws T. Further, the bottom of the adapter cover 21 is provided with a wiring hole 21b for the cables to pass through.

After assembly, since the rotating head 222 has a connecting structure to allow rotation relative to the assembling plate 221, the assembled whole piece of the display unit 1, the adapter cover 21 and the assembling plate 221 can rotate and switch between the transverse and longitudinal directions relative to the rotating head 222, that is, the display unit 1 can rotate in the plane where the display surface is located, and the included angle between the entire display surface and the horizontal plane remains unchanged. In other words, the display unit 1 is fastened and connected to the adapter cover 21 in a way that allows rotation relative to the rotating unit 2.

Further, the support unit 2 may include a support 23 fastened and connected to the rotating head 222. In the specific implementation, one end of the support 23 is hinged to the rotating head 222, so that the assembled whole piece of the display unit 1, the adapter cover 21, the assembling plate 221 and the rotating head 222 can swing left and right in the horizontal direction so as to increase the display viewing angle; and the other end of the support 23 is hinged to another fixed structure of the monitor, so that the support 23 can swing up and down in the vertical direction so as to increase the display viewing angle.

Further, the display unit 1 is switched between the vertical and horizontal directions in a way that allows rotation relative to the rotating unit 2. When the display unit 1 and the master control unit 9 are separately connected and installed in such a way that a long edge 1d of the front side of the display unit is horizontally disposed, the display unit 1 is divided into N display areas parallel to the long edge, and waveforms/values related to parameter information from a patient-end are displayed in at least one of the display areas, as shown in FIG. 5; and when the display unit 1 and the master control unit 9 are separately connected and installed in such a way that a short edge 1c of the front side of the display unit 1 is horizontally disposed, the display unit 1 is divided into M display areas parallel to the short edge 1c, and waveforms/values related to the parameter information from the patient-end are displayed in at least one of the display areas, as shown in FIG. 4.

In one embodiment, the number of the display areas N is less than the number of the display areas M, achieving the advantage of displaying of the display unit in different display directions so as to display more waveforms/values.

Further, the display unit 1 is switched between the horizontal and vertical directions in a way that allows rotation relative to the rotation units 2. When the display unit 1 and the master control unit 9 are separately connected and installed in such a way that the long edge 1d of the front side of the display unit 1 is horizontally disposed, waveforms related to the parameters are displayed in a first time zone. When the display unit 1 and the master control unit 9 are separately connected and installed in such a way that the short edge 1c of the display unit 1 is horizontally disposed, waveforms related to the parameters are displayed in a second time zone, with the first time zone being greater than the second time zone.

Figure 3:
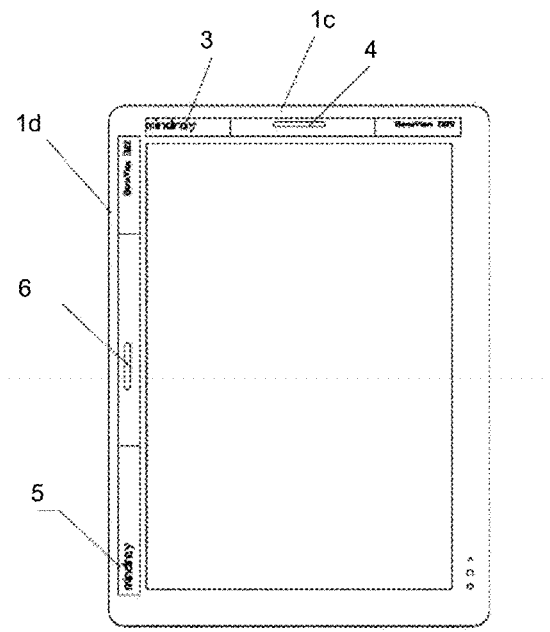
FIG. 3 is a schematic diagram of an internal structure of a display unit of the monitor.
Figure 4:
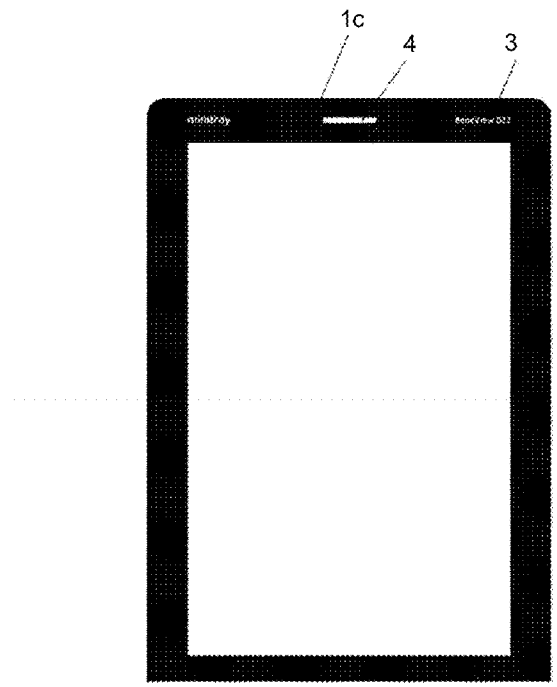
FIG. 4 is a schematic diagram of the display unit of the monitor in a portrait display mode.
Figure 5:
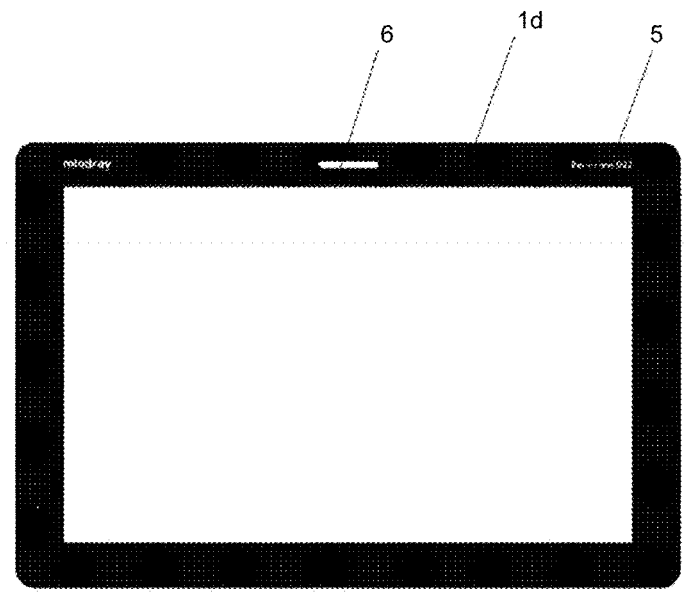
FIG. 5 is a schematic diagram of the display unit of a monitor in a landscape display mode.

As shown in FIGS. 3-5, at the position of the short edge 1c of the front side of the display unit 1, the display unit 1 may be provided with a first marker display area 3 for displaying a marker and an alarm light display area 4 for displaying an alarm light when the display unit 1 and the master control unit 9 are separately connected and installed in such a way that the short edge 1c of the front side of the display unit 1 is horizontally disposed, i.e., when the display unit 1 is in a vertical mode. The display unit 1 is provided with a second marker display area 5 for displaying a marker and an alarm light display area 6 for displaying an alarm light when the display unit 1 and the master control unit 9 are detachably connected and installed in such a way that the long edge 1d of the front side of the display unit 1 is horizontally disposed, i.e., when the display unit 1 is in a transverse mode.

In this embodiment, the first marker display area 3 and the alarm light display area 4 are integrated on a same PCB and at the position of the short edge 1c. The second marker display area 5 and the alarm light display area 6 are integrated on the same PCB, and disposed at the position of the long edge 1d. In the specific implementation, when the display unit 1 rotates and switches between the horizontal and vertical directions by 90 degrees relative to the rotating unit, a gravity sensor arranged in the display unit 1 can identify the horizontal and vertical directions of the screen and further respectively display same through the first marker display area 3 and the alarm light display area or respectively display same through the second first marker display area 5 and the alarm light display area 6.

Basic information may include, but is not limited to, the product identifier/machine model of the monitor. In addition, two independent display systems may be used to respectively control the display conditions of light bars. When the display unit 1 switches to the portrait state, the master control unit 9 controls the first group of marker display areas 3 and/or one alarm light display area 4 to be effective while controlling the second group of marker display areas 5 and/or the alarm light display area 6 to be ineffective. Specifically, by the polarizer technology or by spraying ink, when no product identifier, alarm light or machine model is displayed, the user could hardly detect the marker display area and/or the alarm light display area at the position of the short edge 1c/the long edge 1d.

A long border of the display unit 1 may be provided with a handle 7, which is more convenient for the user to perform rotation and switching between the horizontal and vertical directions.

Figure 6:
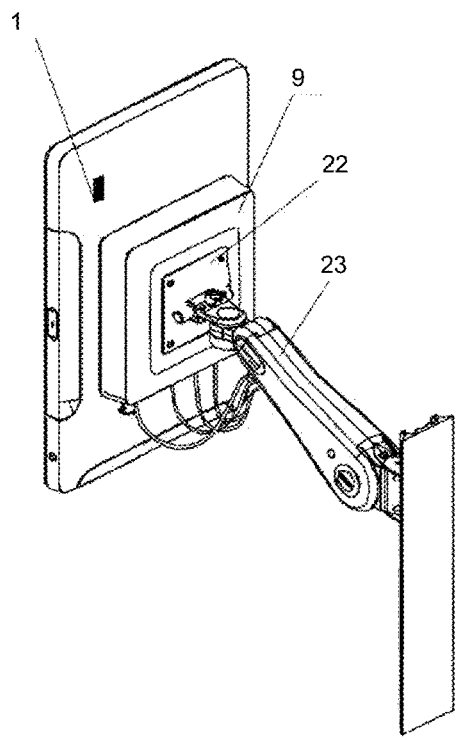
FIG. 6 is a structural schematic diagram of a display unit of a vertically assembled monitor.
Figure 7:
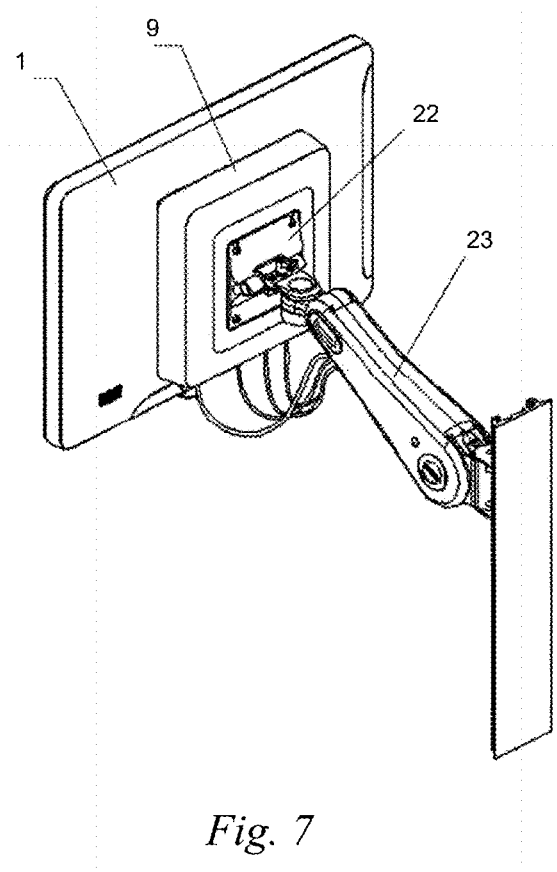
FIG. 7 is a structural schematic diagram of a display unit of a horizontally assembled monitor.

FIGS. 6-7 provide another embodiment of the monitor according to the present disclosure. This embodiment is different from the embodiment disclosed above in that the display unit 1 and the master control unit 9 are not of the aforementioned separate connection structure, but of an integrated detachable structure. During specific implementation, a connection cable (not shown) for data transmission is provided between the master control unit 9 and the display unit 1, and the connection cable is received in the master control unit 9 and the display unit 1.

The detachable structure between the display unit 1 and the master control unit 9 can be implemented in various ways. For example, the back of the display unit 1 may be provided with a plurality of connecting poles (not shown) which are centrosymmetric, the master control unit 9 is provided with assembling holes, the master control unit 9 is fastened to the adapter cover in such a way that the plurality of centrosymmetric connecting poles are adaptively connected with the assembling holes in the transverse or longitudinal direction, which enables the display unit 1 to be assembled on the master control unit 9 in any of the horizontal and longitudinal directions.

In this embodiment, the display unit 1 and the master control unit 9 are of an integrated detachable structure, and when the display unit 1 needs to rotate, the display unit 1 can be disassembled for rotation and then reinstalled. In this process, adjusting the position of the display unit 1 does not affect the position of a cable L, e.g., a power cable, a card cage cable, a subordinative screen cable, a USB connecting cable or a network signal cable, at the bottom of the master control unit 9, and the position of the cable does not change, and the crossing and rolling of cables can be avoided. It also has the advantage of saving on space and facilitating assembly and maintenance.

In this embodiment, in the process of the display unit 1 is switched between the horizontal and vertical directions in a way that allows rotation relative to the rotating unit 2, the display mode of the display unit 1, the application modes of the first marker display area 3, the alarm light display area 4 for displaying an alarm light, the second group of marker display areas, and the alarm light display area 6 are the same as those of the previous embodiment, which will not be repeated here.

In other embodiments of the monitor of the present disclosure, the display unit 1 and the master control unit 9 may also be of an integrated rotatable structure. In the specific implementation, a partial structure of the support unit 2 in the aforementioned Embodiment 1 may be installed between the display unit 1 and the master control unit 9 to enable the display unit 1 to rotate relative to the master control unit 9. For example, the adapter cover 21 can be fastened to the display unit 1, and the rotating unit 22 connected to the adapter cover 21 can be fastened to the master control unit 9. In this way, since the display unit 1 can rotate relative to the rotating unit 22, the integrated rotatable structure between the display unit 1 and the master control unit 9 is realized.

The present disclosure also discloses a monitoring system including the above-mentioned monitor. The specific embodiment is the same as the embodiment of the aforementioned monitor of the present disclosure, which will not be repeated here.

The monitor, the display device thereof, and the monitoring system provided by the present disclosure have the following beneficial effects. First, the display unit and the master control unit are separated from each other, and the display unit is fastened and connected to the support unit in such a way that the display unit allows rotation relative to the rotating unit, so as to achieve the function of switching between transverse and longitudinal rotations. As a result, during the rotation of the display unit, the positions of cables of the master control unit do not change, so as to reduce the problems of entanglement and loosening of cables in clinic. It is possible to prolong the service life of cable interfaces and devices, and improve serviceability.

Second, after rotating and switching, the direction of screen rotation is automatically identified, and corresponding marker display areas and alarm light display areas are lit up in order to taking into consideration habits of a user.

Third, with the integrated structure of the display unit and the master control unit, the used space can be reduced, and screen installation in the landscape or portrait orientation can be provided according to the actual application requirements, and since the positions of cables of the master control unit do not change, the connection mode of a signal line or a power line is not affected.

Fourth, the present disclosure is structurally reasonable, and facilitates assembly and maintenance. The present disclosure is not limited to the above embodiments. For example, the support unit may be not limited to the form of the adapter cover plus the rotating unit. The back of the display unit of the monitor can be provided with a rotating hole which matches the support unit with a rotating shaft to perform rotation, and the display unit and the support unit may also be magnetically connected. In these cases, the support unit may be a support rod, a shaft, or even a fixed wall.

The above-mentioned examples merely represent several embodiments, giving specifics and details thereof, but should not be understood as limiting the scope of the present patent of disclosure thereby. It should be noted that those of ordinary skill in the art would also able to make several alterations and improvements without departing from the spirit of the present disclosure and these would all fall within the scope of protection of the present disclosure. Therefore, the protection scope of the present disclosure shall be subject to appended claims.

What is claimed is:

1. A display device for a patient monitor, comprising a display unit and a support unit, the display unit comprising a display screen for displaying patient-end parameter information, and the display unit being connected to the support unit in a way that allows rotation relative to the support unit, wherein at least one short edge of the display unit is provided with a first alarm light display area for displaying a first alarm light when the display unit is in a vertical mode, and at least one long edge of the display unit is provided with a second alarm light display area for displaying a second alarm light when the display unit is in a transverse mode, and wherein when the display unit is switched to the vertical mode, a master control unit controlling said first alarm light display area to be lighted while the said second alarm light display area to be not lighted, and when the display unit is switched to the transverse mode, the master control unit controlling said first alarm light display area to be not lighted while the said second alarm light display area to be lighted, wherein said first and second alarm light display areas are separate from the display screen.

2. The display device of claim 1, wherein the first alarm light display area and the second alarm light display area are independent display systems, or the first alarm light display area and the second alarm light display area are integrated on different printed circuit boards (PCBs).

3. The display device of claim 2, wherein a rotating unit comprises an assembling plate capable of being fastened to an adapter cover and a rotating head rotatably connected to the assembling plate; the display unit, the adapter cover, the assembling plate and the rotating head are assembled as a whole piece; and the whole piece of the display unit, the adapter cover and the assembling plate rotates and switches between transverse and longitudinal directions relative to the rotating head.

4. The display device of claim 1, wherein the display unit is connected by a cable to the master control unit; and
wherein the master control unit is connected to a parameter sensor through at least one cable.

5. The display device of claim 1, wherein said display unit comprises a concave cavity for assembly, wherein the support unit comprises an adapter cover to be arranged in said concave cavity and a rotating unit connected to the adapter cover, and the display unit is fastened and connected to the adapter cover in a way that allows rotation relative to the rotating unit.

6. The display device of claim 1, wherein the master control unit is separate from, and does not rotate with, the display unit, and
wherein the master control unit is fixedly provided with one or more additional cables including any of a power cable, a card cage cable, a subordinative screen cable, a USB connecting cable, or a network signal cable to be connected to a parameter sensor.

7. A patient monitor, which comprises the display device according to claim 1, the master control unit being used for transmitting parameter information from a patient end to the display unit, and the display unit being used for displaying the parameter information; wherein either:
the master control unit is connected to the patient end through at least one cable, and the display unit being detachably connected to the master control unit; or
the display unit and the master control unit are separated from each other, and the display unit is rotatably installed on the support unit of said display device.

8. The patient monitor of claim 7, wherein when the display unit and the master control unit are installed in such a way that the at least one long edge of the display unit is disposed horizontally, the display unit is divided into N display areas parallel to the at least one long edge, with waveforms/values related to the parameter information being displayed in at least one of the display areas; and when the display unit and the master control unit are installed in such a way that the at least one short edge of the display unit is disposed horizontally, the display unit is divided into M display areas parallel to the at least one short edge, with waveforms/values related to the parameter information being displayed in at least one of the display areas, the number of the display areas N is less than the number of the display areas M.

9. The patient monitor of claim 8, wherein when the display unit and the master control unit are installed in such a way that the at least one long edge of the display unit is disposed horizontally, waveforms related to the parameters are displayed in a first time duration, and when the display unit and the master control unit are installed in such a way that the at least one short edge of the display unit is disposed horizontally, waveforms related to the parameters are displayed in a second time duration, the first time duration being greater than the second time duration.

10. The patient monitor of claim 7, wherein the display unit can be switched between landscape and portrait orientations by rotation, when the display unit is switched between landscape and portrait orientations, the display unit is switched into a display mode to keep the parameter information displayed in the horizontal direction.

11. A display device for a patient monitor, comprising a display unit and a support unit, the display unit comprising a display screen for displaying patient-end parameter information, and the display unit being connected to the support unit in a way that allows rotation relative to the support unit,
wherein at least one short edge of the display unit is provided with a first marker display area when the display unit is in a vertical mode, and at least one long edge of the display unit is provided with a second marker display area when the display unit is in a transverse mode, and wherein, when the display unit is switched to the vertical mode, a master control unit controlling said first marker display area to be lighted while said second marker display area to be not lighted, and when the display unit is switched to the transverse mode, the master control unit controlling said first marker display area to be not lighted while said second marker display area to be lighted, wherein the first and second marker display areas are separate from the display screen.

12. The display device of claim 11, wherein when the display unit is switched to the vertical mode, the master control unit controlling said first marker display area to be displayed while the said second marker display area to be not displayed, and when the display unit is switched to the transverse mode, the master control unit controlling said first marker display area to be not displayed while said second marker display area to be displayed.

13. The display device of claim 12, wherein the first marker display area and the second marker display area are independent display systems, or the first marker display area and the second marker display area are integrated on different printed circuit boards (PCBs).

14. The display device of claim 12, wherein the display unit is connected by a cable to the master control unit; and
wherein the master control unit is connected to a parameter sensor through at least one cable.

15. The display device of claim 12, wherein said display unit comprises a concave cavity for assembly, wherein the support unit comprises an adapter cover to be arranged in said concave cavity and a rotating unit connected to the adapter cover, and the display unit is fastened and connected to the adapter cover in a way that allows rotation relative to the rotating unit.

16. The display device of claim 15, wherein the rotating unit comprises an assembling plate capable of being fastened to the adapter cover and a rotating head rotatably connected to the assembling plate; the display unit, the adapter cover, the assembling plate and the rotating head are assembled as a whole piece; and the assembled whole piece of the display unit, the adapter cover and the assembling plate rotates and switches between transverse and longitudinal directions relative to the rotating head.

17. The display device of claim 12, wherein the master control unit is separate from, and does not rotate with, the display unit, and
wherein the master control unit is fixedly provided with one or more additional cables including any of a power cable, a card cage cable, a subordinative screen cable, a USB connecting cable, or a network signal cable to be connected to a parameter sensor.

18. A patient monitor, which comprises the display device according to claim 1, the master control unit being used for transmitting parameter information from a patient end to the display unit, and the display unit being used for displaying the parameter information;
wherein either:
the master control unit is connected to the patient end through at least one cable, and the display unit being detachably connected to the master control unit; or
the display unit and the master control unit are separated from each other, and the display unit being rotatably installed on a support unit of said display device.

19. The patient monitor of claim 18, wherein when the display unit and the master control unit are installed in such a way that the at least one long edge of the display unit is disposed horizontally, the display unit is divided into N display areas parallel to the at least one long edge, with waveforms/values related to the parameter information being displayed in at least one of the display areas; and when the display unit and the master control unit are installed in such a way that the at least one short edge of the display unit is disposed horizontally, the display unit is divided into M display areas parallel to the at least one short edge, with waveforms/values related to the parameter information being displayed in at least one of the display areas, the number of the display areas N is less than the number of the display areas M.

20. The patient monitor of claim 18, wherein the display unit can be switched between landscape and portrait orientations by rotation, when the display unit is switched between landscape and portrait orientations, the display unit is switched into a display mode to keep the parameter information displayed in the horizontal direction.

* * * * *